United States Patent
Norén et al.

(10) Patent No.: US 6,860,857 B2
(45) Date of Patent: Mar. 1, 2005

(54) IMPLANTABLE INTRAVASCULAR PRESSURE DETERMINING DEVICE AND METHOD

(75) Inventors: Kjell Norén, Solna (SE); Seven-Erik Hedberg, Kungsängen (SE); Kenth Nilsson, Åkersberga (SE)

(73) Assignee: St. Jude Medical AB, Järfälla (SE)

( * ) Notice: Subject to any disclaimer, the term of this patent is extended or adjusted under 35 U.S.C. 154(b) by 90 days.

(21) Appl. No.: 10/078,210

(22) Filed: Feb. 19, 2002

(65) Prior Publication Data

US 2003/0045800 A1 Mar. 6, 2003

(30) Foreign Application Priority Data

Aug. 31, 2001 (SE) .............................................. 0102919

(51) Int. Cl.$^7$ ................................................ A61B 5/00
(52) U.S. Cl. ...................................... 600/486; 600/485
(58) Field of Search ................................ 600/485–503

(56) References Cited

U.S. PATENT DOCUMENTS

| | | | | |
|---|---|---|---|---|
| 4,566,456 A | | 1/1986 | Koning et al. | |
| 5,343,868 A | * | 9/1994 | Kurscheidt et al. | 600/486 |
| 5,899,927 A | * | 5/1999 | Ecker et al. | 607/23 |
| 5,957,853 A | * | 9/1999 | Giuffre | 600/486 |
| 6,026,324 A | | 2/2000 | Carlson | |
| 6,589,184 B2 | * | 7/2003 | Noren et al. | 600/486 |
| 6,592,528 B2 | * | 7/2003 | Amano | 600/485 |
| 6,620,104 B2 | * | 9/2003 | Tamura et al. | 600/485 |

* cited by examiner

Primary Examiner—Robert L. Nasser
(74) Attorney, Agent, or Firm—Schiff Hardin LLP

(57) ABSTRACT

In an implantable intravascular pressure determining device and method, a pressure sensor generates a raw pressure signal and an acceleration sensor measures acceleration in a patient. Time intervals are identified wherein the raw pressure signal accurately represents the intravascular pressure, these intervals being identified as the time intervals wherein the measured acceleration is below a predetermined threshold. The raw pressure signal is processed, to generate a processed signal which is used as an intravascular pressure signal, only in the aforementioned time intervals.

16 Claims, 1 Drawing Sheet

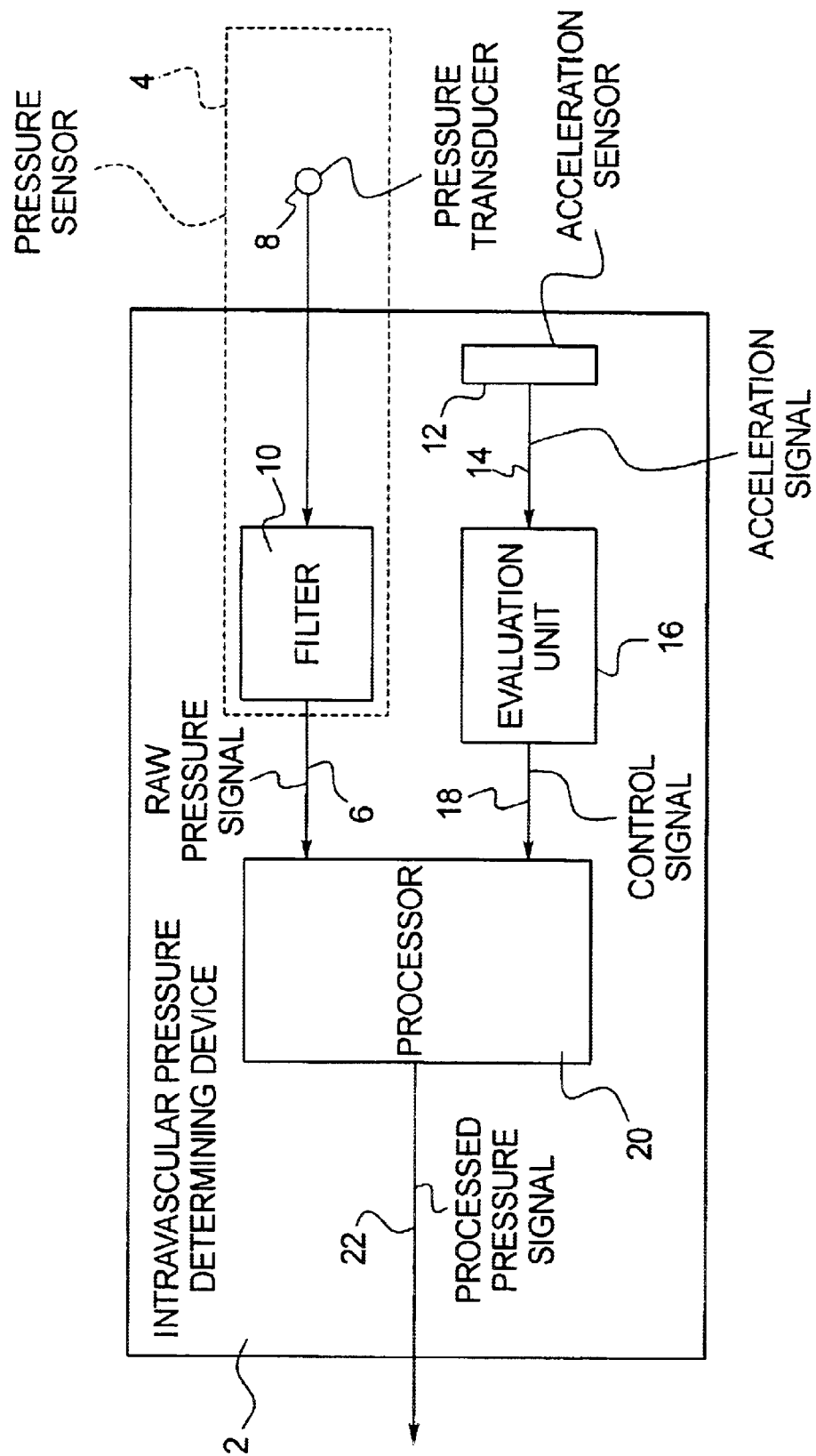

IMPLANTABLE INTRAVASCULAR PRESSURE DETERMINING DEVICE AND METHOD

BACKGROUND OF THE INVENTION

1. Field of the Invention

The present invention relates to an implantable intravascular pressure determining device and method.

2. Description of the Prior Art

A cardiac stimulating apparatus is described in U.S. Pat. No. 6,026,324 that non-intrusively determines a value indicative of hemodynamic pulse pressure from an accelerometer signal obtained by an accelerometer sensor enclosed in an implantable casing of the stimulating apparatus. The accelerometer sensor is electrically coupled to a microprocessor-based controller and the accelerometer transmits a signal to the controller associated with fluid and myocardial accelerations of the patient's heart. A filtering arrangement is coupled to the accelerometer for filtering and conditioning the signal transmitted by the accelerometer to produce a waveform related to a pulse pressure within the patient's heart. In order to remove ancillary information contained in the acceleration signal the signal is transmitted through a series of filters. Thus, the above-referenced United States patent discloses a device capable of non-intrusively (meaning that no sensor needs to be inserted into the heart) determines a waveform related to the pressure and in particular the pulse pressure within a patient's heart.

Measuring pressure inside a heart by inserting a pressure sensor into the heart is well-known in the art. One example is given in the background section of U.S. Pat. No. 6,026,324 where it is referred to U.S. Pat. No. 4,566,456 discloses a device that adjusts the stimulation rate relative to right ventricular systolic pressure. The ventricular systolic pressure is measured by a piezoelectric pressure sensor mounted on lead inserted into the heart, i.e. an intrusive pressure measurement technique.

In order to obtain accurate and reliable measurements of the intracardial pressure it is often preferred to perform pressure measurements by arranging a pressure sensor inside the heart.

Intracardiac pressure is a highly valuable parameter for estimation of cardiac condition and cardiac pumping efficiency. Technically there is no difficulty in placing a pressure sensor in e.g. the right ventricle of a heart.

Although the pressure sensor may give a correct picture of the pressure at the sensor site, however, the pressure measured in an active patient is a summation of pressures having different origins. Apart from the desired component i.e. the pressure originating from the heart's pumping action, the sensor signal will contain pressure components from other sources such as vibration, external and internal sounds and barometric pressure changes.

In this context, it is relevant to note, that an 11 meter elevation in air gives rise to a pressure change of 1 mm of Hg. Also, it should be noted that the blood column in the body (in the actual case mainly the blood column in the heart) generates pressure changes when the body is exposed to exercise and/or vibrations.

This may be summarized by the following relationship:

$$p = d \cdot h \cdot a \quad \text{(Equation 1A)}$$

where p is the pressure change, d is the blood density, h is the blood column height and a is the acceleration. It should be noted that in the relationship it is indicated that h and a are vectors.

The same blood column will likewise give rise to pressure changes during body posture changes according to:

$$p = d \cdot h \cdot g \quad \text{(Equation 1B)}$$

where g is the gravity constant.

External and internal sounds also can make a non-negligible contribution to the pressure signal. Examples of such external sounds are traffic noise and loud music and internal sounds such as coughing, sneezing and snoring.

Taking the above into account, it is fairly difficult to extract the desired signal i.e. the pressure signal emanating solely from the heart's pumping action, from the sensor signal.

For many applications it would be sufficient to measure the cardiac pressure during limited time intervals. One issue is then how to find intervals during which the cardiac pressure signal is the dominating signal contributor.

SUMMARY OF THE INVENTION

An object of the present invention is to extract the cardiac pressure signal from a measured pressure signal obtained by a pressure sensor arranged inside a heart.

Another object of the present invention is to extract the intravascular pressure from a measured pressure signal obtained by a pressure sensor that is arranged in the vascular system of a patient, i.e. in the heart as well as in a blood vessel.

The above object is achieved in accordance with the principles of the present invention in an implantable intravascular pressure determining device, and in a method for determining intravascular pressure, wherein a raw intravascular pressure signal is generated by a pressure sensor adapted for placement in the vascular system of a patient, wherein time intervals are identified in which the raw pressure signal represents the intravascular pressure, these intervals being the time intervals in which a measured acceleration, obtained by an acceleration sensor, is below a predetermined threshold, and wherein the first intravascular pressure signal is processed to generate a processed pressure signal corresponding to the intravascular pressure during the identified time intervals.

Thus, according to the present invention the accuracy of the pressure measurements obtained by a pressure sensor in the vascular system of a patient is increased.

This is generally achieved by identifying time periods where the acceleration is small and therefore the measured pressure represents the "true" intravascular pressure.

DESCRIPTION OF THE DRAWINGS

The FIGURE shows a simplified block-diagram of the implantable intravascular pressure determining device constructed and operating according to the present invention.

DESCRIPTION OF THE PREFERRED EMBODIMENTS

The implantable intravascular pressure determining device 2 shown in the FIGURE has a pressure sensor 4 which generates a raw intravascular pressure signal 6. The pressure sensor 4 has a pressure transducer 8 and a filter 10. The pressure transducer 8 is adapted to be positioned in the vascular system of a patient, e.g. in a blood vessel or inside the heart. According to a preferred embodiment of the invention the pressure transducer 8 is an integral part of an electrode lead that is inserted into the heart and is used to apply stimulation pulses to the heart tissue.

The pressure determining device 2 further has an acceleration sensor 12 for generating an acceleration signal 14 and an evaluation unit 16 for determining a control signal 18 from the acceleration signal 14.

The raw pressure signal 6 and the control signal 18 are applied to a processor 20 which processes the raw pressure signal 6 only in the time interval enabled by the control signal 18, to generate a processed pressure signal 22, that corresponds to the intravascular pressure.

The measured pressure signal generated by the pressure transducer 8 and the acceleration signal 14 need to be filtered. The signal obtained by the pressure transducer 8 is filtered by the filter 10 to obtain the raw pressure signal 6. The filter 10 preferably is a bandpass filter with frequency pass-band in the range between 0.5 and 10 Hz.

The acceleration sensor 12 includes a band-pass filter adapted to filter out the acceleration signal 14. According to a preferred embodiment of the invention it has a similar characteristic as the filter 10.

The evaluation unit 16 and the processor 20 are implemented either by logic circuitry, including amplifying means, or by a combination of a microprocessor and amplifying means.

Those skilled in the art of signal processing are aware of numerous ways of realizing the filtering and among those may be mentioned digitally controlled filters and conventional analog filters.

As briefly discussed above the acceleration sensor 12, which often is incorporated in a pacemaker for activity sensing and rate control, generates the acceleration signal 14, that is a combination of vibration, posture changes, external and internal sounds. This combination of different sources involved may all make contributions to the first intravascular pressure signal 6 that need to be eliminated in order to obtain an intravascular pressure value reflecting the pressure at the measure-site compensated from internal and external disturbances.

The acceleration sensor 12 may be any known implantable accelerometer adapted to generate an acceleration signal. In particular, the accelerometer disclosed in PCT application WO 98/50794 is especially suitable when realizing the present invention. WO-98/50794 discloses an accelerometer including a cantilevered beam with a free end arranged to move. The beam has at least one piezoelectric layer and at least one supporting layer. The free end of the beam is provided with a sensing mass located eccentrically in relation to the longitudinal direction of the beam.

The present invention is applicable to any signal reflecting the pressure in the heart or blood vessel obtained by any type of pressure sensor adapted to be inserted into the heart or into a vessel of a patient. Thus, the pressure sensor 4 to be used in a medical device according to the present invention may in particular be a piezoresistive pressure sensor. Piezoresistive pressure sensors are well-known from the art. For example, U.S. Pat. Nos. 4,566,456 or 5,324,326 disclose a pressure sensor on an integrated circuit chip having a layer of piezoresistive material and a non-conductive base member, with the layer of piezoresistive material being carried by the base member and having a pressure sensing diaphragm area therein exposed to ambient pressure.

Thus, and according to the present invention, if it is possible to measure pressure during intervals when the output from the accelerometer is zero or at least small, it is known that the measured pressure signal consists essentially of the intravascular pressure signal. If the measurement is performed inside the heart the intravascular pressure equals the cardiac pressure.

The following relationship illustrates the present invention by using the embodiment where the pressure sensor is arranged inside a heart:

$$P_{measured} = P_{disturb} + P_{cardiac}$$

where $P_{measured}$ is the pressure measured by a sensor inside the heart, $P_{disturb}$ is the disturbing pressure and $P_{cardiac}$ is the cardiac pressure signal, i.e. the "clean" pressure that is to be determined.

By using the general terms set forth above the first pressure signal 6 is $P_{measured}$, the second pressure signal 18 is $P_{disturb}$ and a third pressure signal is $P_{cardiac}$.

Most of the severely disturbing pressure signals are directly proportional to acceleration according to:

$$P_{disturb} = k \cdot a \qquad \text{(see equations 1A and 1B)}$$

where k is a constant and a is the acceleration. If k is determined, and since a is measured by the accelerometer, then it is possible to determine $P_{disturb}$ that could be subtracted from the measured pressure signal resulting in an essentially clean cardiac pressure signal.

This is the general, basic underlying principle of the present invention, as also disclosed in a related patent application filed simultaneously herewith and issued as U.S. Pat. No. 6,589,104 the teachings of which are incorporated herein by reference. The related patent application discloses, inter alia, different ways to determine the constant k.

The present patent application relates to the specific case when the term $P_{disturb}$ may be disregarded because the value of the acceleration is small.

Returning to the figure the evaluation unit 16 determines time intervals of the acceleration signal having a signal strength below a predetermined threshold.

According to a first preferred embodiment of the present invention the control signal 18 is set to an active state and applied to the processor 20 when the above criterion, i.e. signal strength below a predetermined threshold, is fulfilled. The control signal 18 may e.g. have two different states (0 or 1) where 1 applies when the criterion is fulfilled.

According to a second preferred embodiment of the present invention the control signal 18 indicates and signals relevant state changes of the acceleration signal to the processor, the state changes being the result of predefined signal processing of the acceleration signal 14.

According to a preferred embodiment of the present invention the momentary amplitude of the acceleration signal represents the signal strength, preferably the sampled momentary amplitude value of the acceleration signal.

The thus-determined value of the acceleration signal is compared to the predetermined threshold in the evaluation unit 16 where the predetermined threshold is set to a predetermined part of the maximum signal strength. The predetermined part is preferably set to a value less than 20% of the maximum signal strength. The threshold level is dependent of the accuracy of the measured pressure; the larger error that may be accepted of the pressure to be determined, the higher threshold level may be used.

According to an alternative embodiment of the present invention the fact is used, that the mean value of the acceleration signal may be zero, although the momentary amplitude may be large.

By using the above-mentioned relationships $P_{measured} = P_{disturb} + P_{cardiac}$ and $P_{disturb} = k \cdot a$, the relationship $P_{measured} = k \cdot a + P_{cardiac}$ is formed, where the momentary pressure- and acceleration-values are used.

The relationship is also applicable for the mean values of the measured momentary values during a measurement interval. Thus, $M(P_{measured})=k \cdot M(a)+M(P_{cardiac})$, where "M" designates the mean values of the measured momentary values during a predetermined measurement interval.

This relationship may be used in the following way in order to determine a mean value of the pressure. The acceleration is continuously measured during a number of diastolic intervals of consecutive heart cycles and the mean value of the measured momentary sampled acceleration signal is determined. When the mean value of the acceleration signal is zero or close to zero $M(P_{measured})$ equals $M(P_{cardiac})$, because $M(a)=0$ (or close to zero). This calculation method may be regarded as a "moving window" where the mean acceleration value continuously is determined for a predetermined number of diastolic intervals, e.g. from the latest 30–40 heart cycles. The number should not be too small because then the patient's respiration may influence the measurements. Furthermore the number is not fixed in that it primarily depends on when the mean acceleration value is zero or close to zero.

Thus (during diastole), the measured mean value of the pressure equals the "correct" pressure value provided that the mean acceleration value is zero or close to zero.

The diastolic interval may be identified in many different ways. One way is to use the intracardiac electrogram (if available) and another way is to study the measured pressure that is low during the diastolic phase of the heart cycle. One way to achieve this may be by having the patient walk around for a couple of minutes.

A number of accelerometer signals will occur during diastole. The values from the pressure sensor and the accelerometer sensor means are then compared and used for obtaining a value of the constant k.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable intravascular pressure determining device comprising:
   a pressure sensor adapted for placement in a vascular system of a subject for generating a raw pressure signal;
   an acceleration sensor, separate from said pressure sensor, adapted for measuring acceleration associated with said subject and for generating an acceleration signal corresponding to the measured acceleration, said acceleration signal being separate from said raw pressure signal;
   an evaluation unit supplied with said raw pressure signal and said acceleration signal for identifying time intervals, in which said measured acceleration is below a predetermined threshold, and for generating, a control signal in said time intervals said evaluation unit identifying a maximum signal strength of said acceleration signal, and setting said predetermined threshold to a predetermined fraction of said maximum signal strength; and
   a processor supplied with said raw pressure signal and said control signal for processing said raw pressure signal, to generate a processed signal corresponding to intravascular pressure, only in the time intervals represented by said control signal.

2. An implantable intravascular pressure determining device as claimed in claim 1 wherein said evaluation unit uses an amplitude of said acceleration signal, as a representative of said signal strength, for identifying said maximum signal strength.

3. An implantable intravascular pressure determining device as claimed in claim 1 wherein said evaluation unit samples an amplitude of said acceleration signal, to obtain a sampled momentary value of said acceleration signal, and wherein said evaluation unit uses said sampled momentary value, as a representative of said signal strength, for identifying said maximum signal strength.

4. An implantable intravascular pressure determining device as claimed in claim 1 wherein said evaluation unit repeatedly samples an amplitude of said acceleration signal to obtain a plurality of sampled momentary values, over a plurality of diastolic heart cycles intervals, and wherein said evaluation unit forms an average value of said plurality of sampled momentary values and compares said average value, as a representative of said signal strength, to said predetermined threshold to identify said time intervals.

5. An implantable intravascular pressure determining device as claimed in claim 4 wherein said evaluation unit forms said average value over a plurality of said diastolic heart cycle intervals in a range between 30 and 40.

6. An implantable intravascular pressure determining device as claimed in claim 4 wherein said processor processes said raw pressure signal to generate said processed signal corresponding to said intravascular pressure in at least one of said time intervals wherein said average value is substantially zero.

7. An implantable intravascular pressure determining device as claimed in claim 1 wherein said evaluation unit sets said predetermined threshold at a value which is less than 20% of said maximum signal strength.

8. An implantable intravascular pressure determining device as claimed in claim 1 further comprising an implantable heart stimulating device which is adapted to administer heart stimulating therapy to said subject, and wherein said implantable heart stimulating device generates said heart stimulating therapy dependent on said intravascular pressure indicated by said processed signal.

9. An implantable intravascular pressure determining device as claimed in claim 1 wherein said pressure sensor comprises a pressure transducer which generates a measured pressure signal and a filter supplied with said measured pressure signal for filtering said measured pressure signal to generate said raw pressure signal, and a cardiac electrode, adapted for insertion in a heart, in which said pressure transducer is disposed.

10. A method for determining intravascular pressure, comprising the steps of:
    placing a pressure sensor in a vascular system of a subject and generating a raw pressure signal therewith;
    placing an acceleration sensor, separate from said pressure sensor, in interacting relation with said subject and generating an acceleration signal representing acceleration experience by said subject, said acceleration signal being separate from said raw pressure signal;
    identifying time intervals in which said raw signal accurately represents intravascular pressure, in which time intervals said acceleration signal is below a predetermined threshold;
    identifying a maximum signal strength of said acceleration signal and setting said predetermined threshold as a predetermined fraction of said maximum signal strength; and
    processing said raw pressure signal only in said time intervals to generate a processed signal corresponding to said intravascular pressure in said time intervals.

11. A method as claimed in claim 10 comprising using an amplitude of said acceleration signal as a representative of said signal strength for identifying said maximum signal strength.

12. A method as claimed in claim 10 comprising sampling an amplitude of said acceleration signal to obtain a sampled momentary value, and using said sampled momentary value as a representative of said signal strength for identifying said maximum signal strength.

13. A method as claimed in claim 10 comprising repeatedly sampling said acceleration signal to obtain a plurality of sampled momentary values, averaging said sampled momentary values to obtain a mean value, and using said mean value as a representative of said signal strength for identifying said maximum signal strength.

14. A method as claimed in claim 10 comprising setting said predetermined threshold to a value which is less than 20% of said maximum signal strength.

15. A method as claimed in claim 10 comprising adapting a heart stimulating therapy dependent on said intravascular pressure, and administering said heart stimulating therapy to said subject using an implantable heart stimulating device.

16. A method as claimed in claim 10 comprising generating said raw pressure signal with pressure sensor comprising a pressure transducer which generates a measured pressure signal, and a filter supplied with said measured pressure signal which filters measured pressure signal to generate said raw pressure signal, and inserting said pressure transducer in a heart as a part of a cardiac electrode.

* * * * *